(12) United States Patent
Matsuda et al.

(10) Patent No.: US 7,301,162 B2
(45) Date of Patent: *Nov. 27, 2007

(54) PARTICLE BEAM IRRADIATION SYSTEM

(75) Inventors: Koji Matsuda, Hitachi (JP); Takahide Nakayama, Nara (JP)

(73) Assignee: Hitachi, Ltd., Tokyo (JP)

( * ) Notice: Subject to any disclaimer, the term of this patent is extended or adjusted under 35 U.S.C. 154(b) by 88 days.

This patent is subject to a terminal disclaimer.

(21) Appl. No.: 11/273,392

(22) Filed: Nov. 15, 2005

(65) Prior Publication Data

US 2006/0102856 A1 May 18, 2006

(30) Foreign Application Priority Data

Nov. 16, 2004 (JP) .............................. 2004-331325

(51) Int. Cl.
*G21K 5/10* (2006.01)
*G21G 5/00* (2006.01)

(52) U.S. Cl. ............................. 250/505.1; 250/493.1; 250/492.3; 250/491.1

(58) Field of Classification Search ................ None
See application file for complete search history.

(56) References Cited

U.S. PATENT DOCUMENTS

| 6,316,776 | B1 | 11/2001 | Hiramoto et al. | |
|---|---|---|---|---|
| 6,984,835 | B2 * | 1/2006 | Harada | 250/505.1 |
| 2006/0022153 | A1 * | 2/2006 | Matsuda et al. | 250/493.1 |

FOREIGN PATENT DOCUMENTS

| EP | 0 779 081 A2 | 6/1997 |
|---|---|---|
| EP | 1 477 206 A1 | 11/2004 |
| JP | 2833602 | 10/1998 |

OTHER PUBLICATIONS

Eros Pedroni et al., "The 200-MeV Proton Therapy Project at the Paul Scherrer Institute: Conceptual Design and Practical Realization," Medical Physics, vol. 22, No. 1, Jan. 1995, pp. 37-53.

\* cited by examiner

*Primary Examiner*—Nikita Wells
(74) *Attorney, Agent, or Firm*—Dickstein Shapiro LLP

(57) ABSTRACT

A particle beam irradiation system capable of ensuring a more uniform dose distribution at an irradiation object even when a certain time is required from output of a beam extraction stop signal to the time when extraction of a charged particle beam from an accelerator is actually stopped. The particle beam irradiation system comprises a synchrotron, an irradiation device including scanning magnets and outputting an ion beam extracted from the synchrotron, and a control unit. The control unit stops the output of the ion beam from the irradiation device in accordance with the beam extraction stop signal, controls the scanning magnets to change an exposure position in a state in which the output of the ion beam is stopped, and after the change of the exposure position, starts the output of the ion beam from the irradiation device again. The control unit further outputs a next beam extraction stop signal when an increment of dose integrated from the time of a preceding beam extraction stop signal as a start point reaches a setting dose stored in advance.

20 Claims, 14 Drawing Sheets

FIG.4

| SLICE | X-POSITION | Y-POSITION | TARGET DOSE | SLICE CHANGE FLAG |
|---|---|---|---|---|
| 1 | −10 | −4.5 | 70 | 0 |
| 1 | −9 | −4.5 | 140 | 0 |
| ⋮ | ⋮ | ⋮ | ⋮ | ⋮ |
| 1 | 9 | −4.5 | 1400 | 0 |
| 1 | 10 | −4.5 | 1470 | 0 |
| 1 | 10 | −3.5 | 1540 | 0 |
| 1 | 9 | −3.5 | 1610 | 0 |
| ⋮ | ⋮ | ⋮ | ⋮ | ⋮ |
| 1 | −9 | −3.5 | 2870 | 0 |
| 1 | −10 | −3.5 | 2940 | 0 |
| 1 | −10 | −2.5 | 3010 | 0 |
| ⋮ | ⋮ | ⋮ | ⋮ | ⋮ |
| 1 | −10 | 4.5 | 14700 | 1 |
| 2 | −10 | −4.5 | 14725 | 0 |
| 2 | −9 | −4.5 | 14750 | 0 |
| ⋮ | ⋮ | ⋮ | ⋮ | ⋮ |
| 2 | 9 | −4.5 | 15200 | 0 |
| 2 | 10 | −4.5 | 15225 | 0 |
| 2 | 10 | −3.5 | 15250 | 0 |
| 2 | 9 | −3.5 | 15275 | 0 |
| ⋮ | ⋮ | ⋮ | ⋮ | ⋮ |
| 2 | −9 | −3.5 | 15725 | 0 |
| 2 | −10 | −3.5 | 15750 | 0 |
| 2 | −10 | −2.5 | 15775 | 0 |
| ⋮ | ⋮ | ⋮ | ⋮ | ⋮ |
| 2 | −10 | 4.5 | 19950 | 1 |
| 3 | −10 | −4.5 | 19968 | 0 |
| 3 | −9 | −4.5 | 19986 | 0 |
| ⋮ | ⋮ | ⋮ | ⋮ | ⋮ |
| 3 | 9 | −4.5 | 20310 | 0 |
| 3 | 10 | −4.5 | 20328 | 0 |
| 3 | 10 | −3.5 | 20346 | 0 |
| 3 | 9 | −3.5 | 20364 | 0 |
| ⋮ | ⋮ | ⋮ | ⋮ | ⋮ |
| ⋮ | ⋮ | ⋮ | ⋮ | ⋮ |

FIG.11

| SLICE | X-POSITION | Y-POSITION | TARGET DOSE | SLICE CHANGE FLAG |
|---|---|---|---|---|
| 1 | −10 | −4.5 | 70 | 0 |
| 1 | −9 | −4.5 | 70 | 0 |
| ⋮ | ⋮ | ⋮ | ⋮ | ⋮ |
| 1 | 9 | −4.5 | 70 | 0 |
| 1 | 10 | −4.5 | 70 | 0 |
| 1 | 10 | −3.5 | 70 | 0 |
| 1 | 9 | −3.5 | 70 | 0 |
| ⋮ | ⋮ | ⋮ | ⋮ | ⋮ |
| 1 | −9 | −3.5 | 70 | 0 |
| 1 | −10 | −3.5 | 70 | 0 |
| 1 | −10 | −2.5 | 70 | 0 |
| ⋮ | ⋮ | ⋮ | ⋮ | ⋮ |
| 1 | −10 | 4.5 | 70 | 1 |
| 2 | −10 | −4.5 | 25 | 0 |
| 2 | −9 | −4.5 | 25 | 0 |
| ⋮ | ⋮ | ⋮ | ⋮ | ⋮ |
| 2 | 9 | −4.5 | 25 | 0 |
| 2 | 10 | −4.5 | 25 | 0 |
| 2 | 10 | −3.5 | 25 | 0 |
| 2 | 9 | −3.5 | 25 | 0 |
| ⋮ | ⋮ | ⋮ | ⋮ | ⋮ |
| 2 | −9 | −3.5 | 25 | 0 |
| 2 | −10 | −3.5 | 25 | 0 |
| 2 | −10 | −2.5 | 25 | 0 |
| ⋮ | ⋮ | ⋮ | ⋮ | ⋮ |
| 2 | −10 | 4.5 | 25 | 1 |
| 3 | −10 | −4.5 | 18 | 0 |
| 3 | −9 | −4.5 | 18 | 0 |
| ⋮ | ⋮ | ⋮ | ⋮ | ⋮ |
| 3 | 9 | −4.5 | 18 | 0 |
| 3 | 10 | −4.5 | 18 | 0 |
| 3 | 10 | −3.5 | 18 | 0 |
| 3 | 9 | −3.5 | 18 | 0 |
| ⋮ | ⋮ | ⋮ | ⋮ | ⋮ |
| ⋮ | ⋮ | ⋮ | ⋮ | ⋮ |

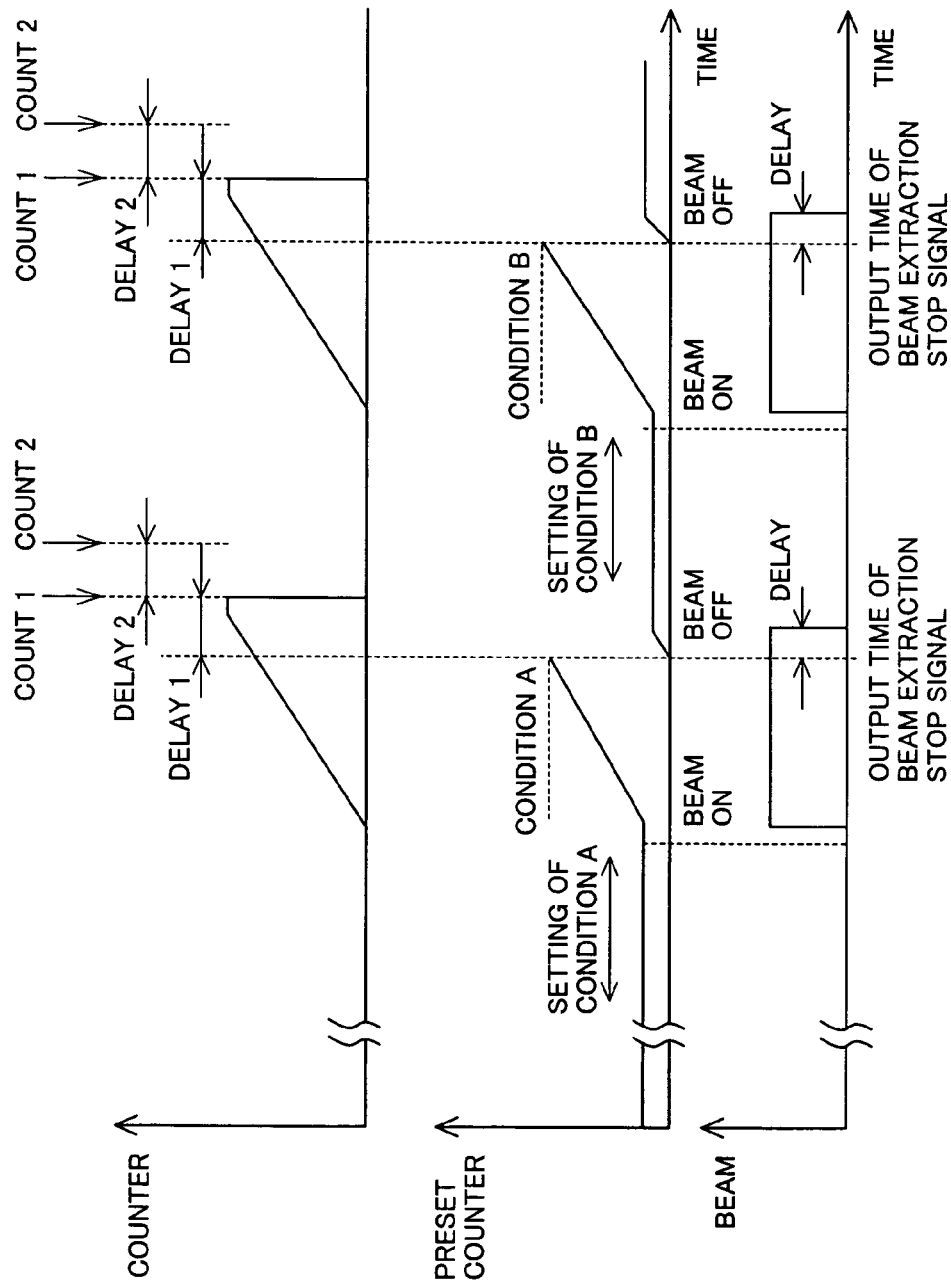

PARTICLE BEAM IRRADIATION SYSTEM

BACKGROUND OF THE INVENTION

1. Field of the Invention

The present invention relates to a particle beam irradiation system, and more particularly to a particle beam irradiation system for irradiating a charged particle beam, such as a proton or carbon ion beam, to an affected part of the body for treatment.

2. Description of the Related Art

There is known a therapy method of irradiating a charged particle beam (ion beam), such as a proton or carbon ion beam, to an affected part, e.g., a cancer, in the body of a patient. A particle beam irradiation system for use with such a therapy method comprises a charged particle beam generator, a beam line, and a treatment room. The charged particle beam accelerated by an accelerator in the charged particle beam generator reaches an irradiation device in the treatment room through the beam line, and it is irradiated to the affected part of the patient body from the irradiation device after being scanned by a scanning magnet disposed in the irradiation device. In that type irradiation system, it has also hitherto been known to stop output of the charged particle beam from the irradiation device, to change (scan) an exposure position (spot) of the charged particle beam by controlling the scanning magnet in the state where the output of the charged particle beam is stopped, and after the change of the exposure position, to start the output of the charged particle beam again from the irradiation device (see, e.g., Patent Document 1; Japanese Patent No. 2833602 (FIG. 1, etc.))

SUMMARY OF THE INVENTION

In the known particle beam irradiation system described above, a dose monitor for measuring a beam dose distribution and a beam position monitor are disposed within the irradiation device at a position downstream of the magnet and immediately upstream of the patient as an irradiation object (target) so that exposure to normal tissue is minimized and irradiation therapy is performed in a normal manner without causing excess or deficient dose.

In irradiation to each spot, a target dose is set per spot. When an integrated value of dose detected by the dose monitor reaches the target dose, a beam extraction stop signal is outputted to the accelerator, whereupon the accelerator stops extraction of the charged particle beam. However, the inventors have found a possibility that, in the accelerator, a slight response delay occurs after the input of the beam extraction stop signal to the accelerator. In the case employing a synchrotron that is one type of accelerators, ions introduced from a pre-stage accelerator and having low energy are circulated within the synchrotron, and the circulating charged particle beam is accelerated up to a setting energy desired to the irradiation, and the accelerated charged particle beam is brought to a resonated state of betatron oscillation. Then, an RF electromagnetic field is applied to the circulating charged particle beam to increase the betatron oscillation of the charged particle beam in excess of the separatix, thereby extracting the charged particle beam. As a result, even with the beam extraction stop signal inputted as mentioned above, the extraction of the charged particle beam is not stopped at once in the strict sense and a slight response delay occurs. Stated another way, even after reaching the target dose, the charged particle beam is continuously irradiated to the relevant spot for the response delay time.

Accordingly, an object of the present invention is to provide a particle beam irradiation system capable of ensuring a more uniform dose distribution at an irradiation object.

To achieve the above object, the present invention is featured in that, when the sum of a first dose irradiated after output of a beam extraction stop signal with respect to a first exposure position preceding a second exposure position and a second dose irradiated to the second exposure position reaches a setting dose, the beam extraction stop signal is outputted to stop the extraction of the charged particle beam irradiated to the second exposure position.

With the present invention, when the sum of the first dose and the second dose reaches the setting dose, the beam extraction stop signal is outputted to stop the extraction of the charged particle beam irradiated to the second exposure position. Therefore, the dose irradiated to the first exposure position during a period in which the extraction of the charged particle beam from the accelerator is actually stopped after the output of the beam extraction stop signal can be added to the dose measured as being irradiated to the second exposure position. As a result, the dose irradiated to each exposure position can be held substantially equal to the setting dose, and a dose distribution at the irradiation object can be made more uniform even when a certain time is required from the output of the beam extraction stop signal to the time when the extraction of the charged particle beam from the accelerator is actually stopped.

Preferably, the control unit determines the presence of an abnormality based on the dose irradiated to the first exposure position during the period from the output of the beam extraction stop signal to the stop of extraction of the charged particle beam from the accelerator. With the determination on the presence of an abnormality, it is possible to reliably confirm that the extraction of the charged particle beam from the accelerator is stopped without failures after the output of the beam extraction stop signal.

Thus, according to the present invention, a dose distribution at the irradiation object can be made more uniform even when a certain time is required from the output of the beam extraction stop signal to the time when the extraction of the charged particle beam from the accelerator is actually stopped.

BRIEF DESCRIPTION OF THE DRAWINGS

FIG. 4 is a table showing details of command signals used in the first embodiment for carrying out scanning in each slice when irradiation is performed in accordance with a treatment plan planned by a treatment planning system shown in FIG. 1;

FIG. 11 is a table showing details of command signals used for carrying out scanning in each slice when irradiation is performed in accordance with a treatment plan planned by a treatment planning system in a proton beam irradiation system according to a second embodiment of the present invention;

FIG. 14 is a timing chart showing one example of counters and actual beam operation realized with the control procedures, shown in FIG. 13, executed by the scanning controller in the second embodiment.

DESCRIPTION OF THE PREFERRED EMBODIMENTS

A particle beam irradiation system according to a first embodiment of the present invention will be described below with reference to the drawings.

Figure 1:
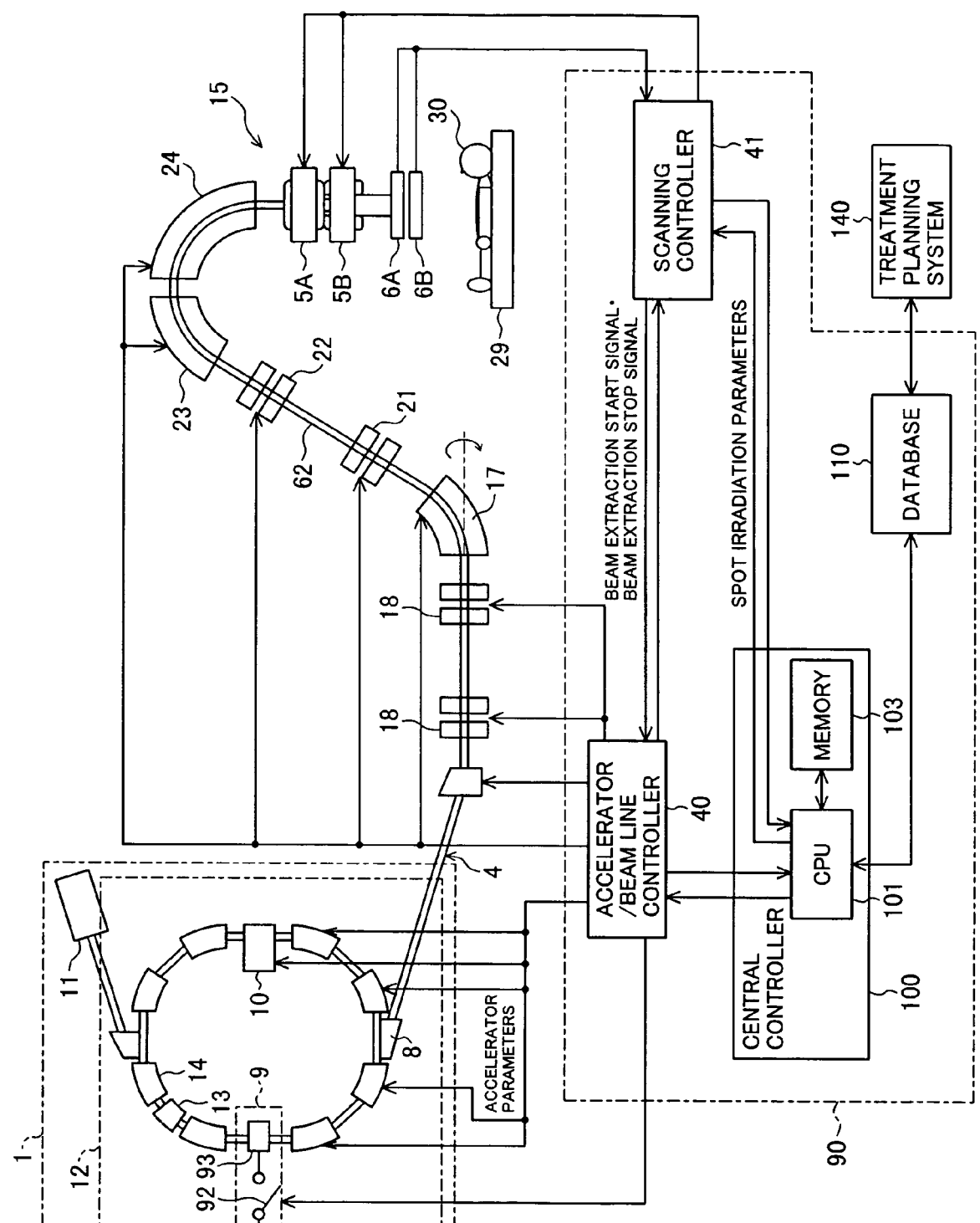
FIG. 1 is a conceptual block diagram showing an overall construction of a proton beam irradiation system, i.e., one example of a particle beam irradiation system, according to a first embodiment of the present invention.

As shown in FIG. 1, a proton beam irradiation system, i.e., one example of the particle beam irradiation system according to the first embodiment of the present invention, comprises a charged particle beam generator 1 and a beam line 4 connected downstream of the charged particle beam generator 1.

The charged particle beam generator 1 comprises an ion source (not shown), a pre-stage charged particle beam generator (linac) 11, and a synchrotron (accelerator) 12. The synchrotron 12 comprises an RF knockout device 9 and an accelerating unit 10. The RF knockout device 9 includes an RF knockout electrode 93 disposed in a circulating orbit in the synchrotron 12 and an RF power supply 91, which are connected to an on/off switch 92. The accelerating unit 10 includes an RF cavity (not shown) disposed in the circulating orbit, and an RF power supply (not shown) for applying RF power to the RF cavity. Ions (e.g., protons or carbon ions) generated from the ion source are accelerated by the pre-stage charged particle beam generator (e.g., a linear charged particle beam generator) 11. An ion beam (proton beam) emitted from the pre-stage charged particle beam generator 11 enters the synchrotron 12. The ion beam in the form of a charged particle beam is accelerated in the synchrotron 12 in which energy is given to the ion beam with RF power applied from the RF power supply through the RF cavity. After energy of the ion beam circulating in the synchrotron 12 has been increased up to a setting level (e.g., 100-200 MeV), an RF wave for beam extraction is supplied from the RF power supply 91 to the RF knockout electrode 93 through the closed on/off switch 92 and is applied to the circulating ion beam from the RF knockout electrode 93. With the application of the RF wave, the ion beam circulating within a separatrix is forced to transit to the outside of the separatrix and to exit from the synchrotron 12 through a beam extraction deflector 8. At the time of extracting the ion beam, currents supplied to a quadrupole magnet 13 and bending magnets 14, which are disposed in the synchrotron 12, are held at current setting values, and therefore the separatrix is also held substantially constant. The extraction of the ion beam from the synchrotron 12 is stopped by opening the on/off switch 92 and ceasing the application of the RF power to the RF knockout electrode 93.

The ion beam extracted from the synchrotron 12 is transported to the downstream side through the beam line 4. The beam line 4 includes quadrupole magnets 18 and a bending magnet 17, and also includes a quadrupole magnet 21, a quadrupole magnet 22, a bending magnet 23 and a bending magnet 24 which are successively arranged on a beam path 62 in this order from the upstream side in the direction of beam advance. The beam path 62 is communicated with an irradiation device 15 disposed in the treatment room. The ion beam introduced to the beam line 4 is transported to the irradiation device 15 through the beam path 62.

The treatment room includes the irradiation device 15 mounted to a rotating gantry (not shown) that is installed inside the treatment room. The irradiation device 15 and a beam transport, which has an inverted U-shape and includes a part of the beam path 62 in the beam line 4, are mounted to a substantially cylindrical rotating drum (not shown) of the rotating gantry (not shown). The rotating drum is rotatable by a motor (not shown). A treatment cage (not shown) is formed inside the rotating drum.

The irradiation device 15 has a casing (not shown) mounted to the rotating drum and connected to the inverted U-shaped beam transport. Scanning magnets 5A, 5B for scanning the beam, a dose monitor (dose detector) 6A, a position monitor 6B, etc. are disposed inside the casing. The Scanning magnets 5A, 5B bend the beam, by way of example, in directions (X- and Y-directions) orthogonal to each other on a plane that is vertical to an axis of the beam, thereby moving the exposure position in the X- and Y-directions.

Before irradiating the ion beam from the irradiation device 15, a treatment bed 29 is moved by a bed driver (not shown) to be inserted in the treatment cage, and is then properly positioned to be ready for the irradiation of the ion beam from the irradiation device 15. The rotating drum is rotated by controlling the rotation of the motor with a gantry controller (not shown) so that the beam axis of the irradiation device 15 is directed to an affected part in the body of a patient 30. The ion beam introduced from the inverted U-shaped beam transport to the irradiation device 15 through the beam path 62 is sequentially scanned in its position for irradiation by the scanning magnets (charged particle beam scanner) 5A, 5B and is irradiated to the affected part (area where a cancer or tumor is generated) in the body of the patient 30. The ion beam releases the energy in the affected part of the patient body to form a high dose region. The scanning magnets 5A, 5B in the irradiation device 15 are controlled by a scanning controller 41 that is disposed in, e.g., a gantry room inside a treatment system.

A control system 90 installed in the proton beam irradiation system of this embodiment will be described with reference to FIG. 1. The control system 90 comprises a central controller 100, a storage (database) 110 for storing treatment plan information, the scanning controller 41, and an accelerator/beam line controller (referred to as an "accelerator controller") 40. Further, the proton beam irradiation system of this embodiment includes a treatment planning system 140.

The treatment plan information (patient information) stored in the storage 110 per patient contains, though not specifically shown, data such as the patient ID number, dose (per irradiation), irradiation energy, irradiating direction, and exposure position.

The central controller 100 comprises a CPU 101 and a memory 103. The CPU 101 reads the treatment plan information regarding the patient, who is now going to take the treatment, out of the storage 110 by using the patient ID information inputted to the CPU. Of the treatment plan information per patient, the value of irradiation energy decides a control pattern for excitation power supplied to the above-mentioned various magnets.

The memory 103 stores a power supply control table in advance. More specifically, corresponding to various values (70, 80, 90, etc. [Mev]) of the irradiation energy, for example, values or patterns of excitation power are set in advance which are supplied to the quadrupole magnet 13 and the bending magnet 14 in the charged particle beam generator 1 including the synchrotron 12, and to the quadrupole magnets 18, the bending magnet 17, the quadrupole magnets 21, 22 and the bending magnets 23, 24 in the beam line 4.

Also, the CPU 101 serves as a control information preparing unit and, by using the treatment plan information and the power supply control table, it prepares control command data (control command information) for controlling the magnets, which are disposed in the charged particle beam generator 1 and in the beam paths, regarding the patient who is now going to take the treatment. Then, the CPU 101 outputs the thus-prepared control command data to the scanning controller 41 and the accelerator controller 40.

In the proton beam irradiation system of this embodiment, the central controller 100, the scanning controller 41, and the accelerator controller 40 execute control in a cooperated manner based on the treatment plan information prepared by the treatment planning system 140. With that control, the extraction of the ion beam from the synchrotron 12 is stopped, and the scanning magnets 5A, 5B are scanned to change the exposure position (spot) of the ion beam in the state where the extraction of the ion beam is stopped. After the change of the exposure position, the extraction of the ion beam from the synchrotron 12 is started. The stop of the extraction of the ion beam from the synchrotron 12 stops the irradiation of the ion beam from the irradiation device 15, and the extraction of the ion beam from the synchrotron 12 starts the irradiation of the ion beam from the irradiation device 15.

Details of the cooperated control executed by the controllers will be described in detail below with reference to FIGS. 2-10.

Figure 2:
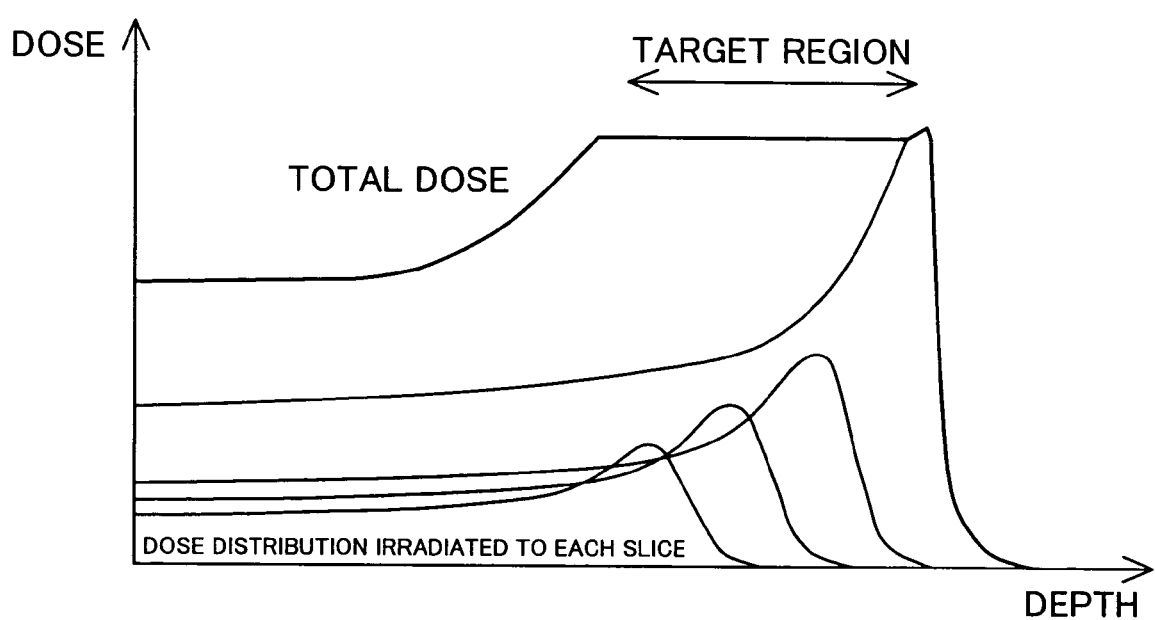
FIG. 2 is a graph showing one example of a dose distribution irradiated for each slice to ensure uniformity in the region of an affected part in the body.

First, the relationship between the depth of a target and the energy of the ion beam is described. The target is a region of an irradiation object including the affected part of the body where the ion beam is to be irradiated, and it is slightly larger than the affected part of the body. FIG. 2 shows, by way of example, the relationship between the depth into the body and the dose irradiated by the ion beam. A peak shown in FIG. 2 is called the Bragg peak. The irradiation of the ion beam to the target is performed at a position of the Bragg peak. The position of the Bragg peak is changed depending on the energy of the ion beam. Accordingly, the ion beam can be uniformly irradiated to the whole of the target (target region) having a thickness in the direction of depth into the body by dividing the target into a plurality of slices (layers) in the direction of depth into the body (i.e., the direction in which the ion beam advances in the body), and by changing the energy of the ion beam depending on the depth (each slice). From that point of view, the treatment planning system 140 decides the number of slices into which the target region is to be divided in the direction of depth into the body.

Figure 3:
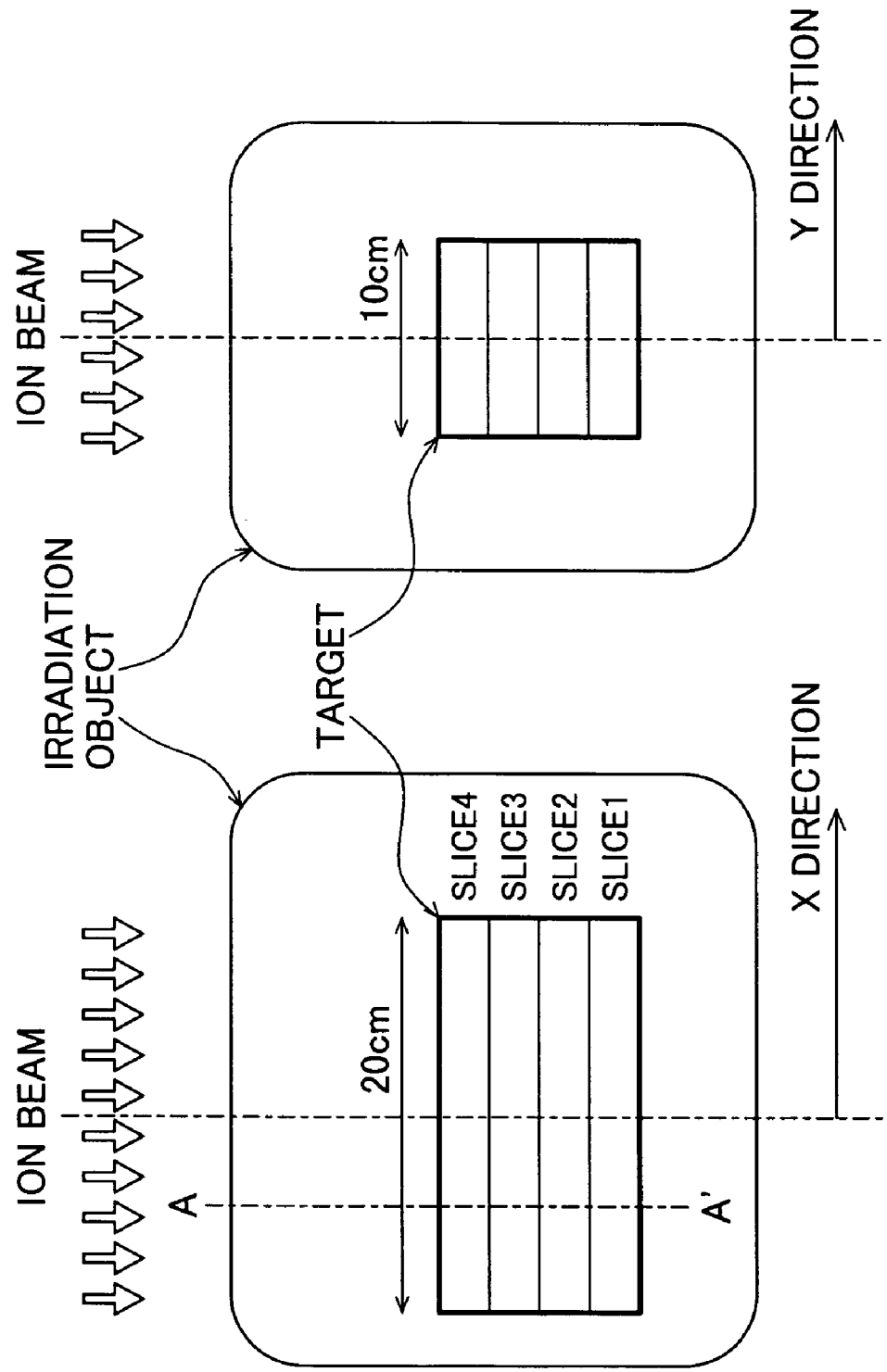
FIG. 3 is an illustration showing one example of the region of the affected part in the body as an irradiation object of the proton beam irradiation system shown in FIG. 1.

FIG. 3 shows one example of the slices decided as described above. In the example of FIG. 3, the affected part of the body is divided into four slices, i.e., slices 1, 2, 3 and 4, from the lowermost slice toward the body surface of the patient 30. Each slice has dimensions of 20 cm in the X-direction and 10 cm in the Y-direction. The dose distribution of FIG. 2 represents the dose distribution in the direction of depth into the body taken along the section A-A' in FIG. 3.

Further, the treatment planning system 140 decides the spot position in a direction perpendicular to the direction of depth into the body within each slice (target cross-section) and the dose irradiated to each spot so that a dose distribution suitable for the treatment is formed.

Then, the treatment plan information planned and stored in the storage 110 as described above is read out by the central controller 100 and stored in the memory 103. Based on the treatment plan information stored in the memory 103, the CPU 101 prepares the information regarding irradiation of the ion beam (such as the number of slices, the number of exposure positions (number of spots), the exposure positions in each slice, the target dose (setting dose) at each exposure position, the values of currents supplied to the scanning magnets 5A, 5B for all the spots in each slice), and then transmits the prepared information to the scanning controller 41. Here, the target dose (setting dose) at each exposure position is defined as integrated exposure dose (integrated dose) measured from the start of the first irradiation to the affected part of the body. Accordingly, when the treatment plan information sets the dose for each of the exposure positions, the central controller 100 successively integrates the individual doses set for the exposure positions, thereby preparing the target dose information to be transmitted to the scanning controller 41. The scanning controller 41 stores the treatment plan information in a memory 41M1 (see FIG. 6). Also, the CPU 101 transmits all the data of accelerator parameters for the synchrotron 12 regarding all the slices, which are contained in the treatment plan information, to the accelerator controller 40. The data of accelerator parameters contain the current values for excitation of the various magnets in the synchrotron 12 and the beam line, as well as the RF power value applied to the RF cavity, which are decided depending on the energy of the ion beam irradiated to each slice. Those data of accelerator parameters are grouped into, for example, a plurality of acceleration patterns in advance.

A part of the treatment plan information stored in the memory 41M1 of the scanning controller 41 will be described with reference to FIG. 4. The part of the information contains irradiation parameters, i.e., information regarding the X-directional position (X-position) and the Y-directional position (Y-position) for each exposure position in the slice, and the target dose (setting dose) at each exposure position. The part of the information also contains information regarding a slice change flag. For all the spots in each slice, the spot numbers (spot number j described later) are assigned in the order of irradiations to those spots. In this embodiment, the dose for each exposure position is set to 70 in the first slice, 25 in the second slice and 18 in the third slice, respectively. The target dose is given as a value obtained by integrating those individual doses in the order of irradiations.

Figure 5:
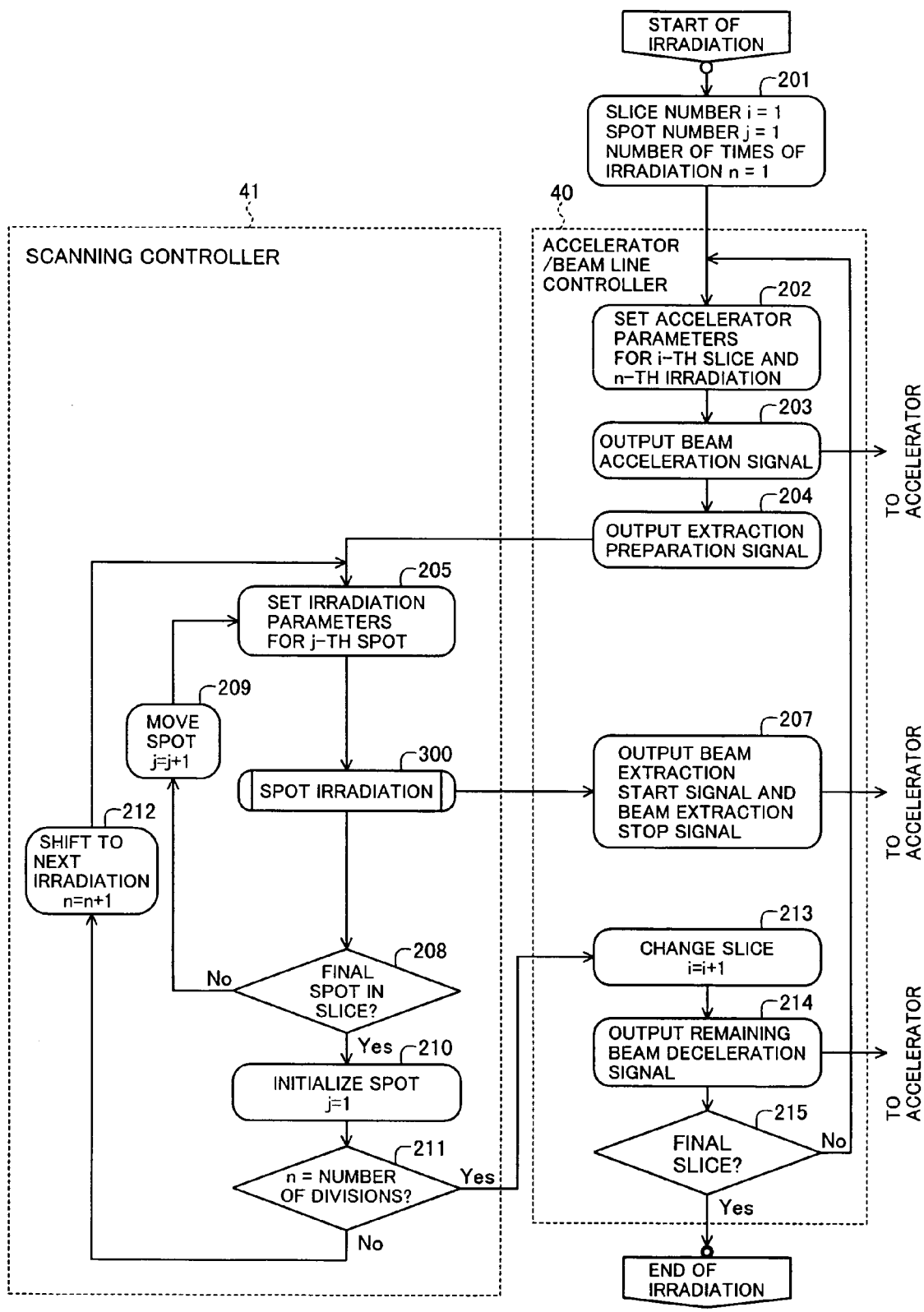
FIG. 5 is a flowchart showing control procedures executed by a scanning controller and an accelerator/beam line controller shown in FIG. 1.

With reference to FIG. 5, a more concrete description is made of control processes executed by the scanning controller 41 and the accelerator controller 40 when spot scanning is performed in this embodiment.

When an irradiation start instructing unit (not shown) disposed in the treatment room is operated, the accelerator controller 40 initializes an operator i representing the slice number to 1 and an operator j representing the spot number to 1 in step 201. After the end of the initialization in step 201, the accelerator controller 40 reads and sets, from among the plural patterns of accelerator parameters stored in the memory, one pattern of accelerator parameters corresponding to the i-th (i=1 at this time) slice in step 202, and then outputs those set accelerator parameters to the synchrotron 12 in step 203. More specifically, in step 203, the accelerator controller 40 outputs, to respective power supplies for the various magnets in the synchrotron 12 and the beam line 4, the information regarding the excitation currents for those magnets, which is contained in the i-th pattern of accelerator parameters, and then controls the respective power supplies so that the relevant magnets are excited by the predetermined currents in accordance with the excitation current information. Also, in step 203, the accelerator controller 40 controls the RF power supply for applying RF power to the RF cavity, thereby increasing the RF power and the frequency to predetermined values. As a result, the energy of the ion beam circulating within the synchrotron 12 is increased to the value decided in the treatment plan. Then, the accelerator controller 40 advances to step 204 in which it outputs an extraction preparation signal to the scanning controller 41.

After receiving the information initialized in step 201 and the extraction preparation signal outputted in step 204 from the accelerator controller 40, the scanning controller 41 reads and sets, in step 205, the current value data and the target dose data for the j-th (j=1 at this time) spot from among the current value data (i.e., data put in columns "X-position" and "Y-position" of FIG. 4) and the target dose data (i.e., data put in column "target dose" of FIG. 4), which are already stored in the memory 41M1 as described above (see also FIG. 6 described later). Similarly, for the later-described target count number stored in the memory 41M1, data corresponding to the j-th (j=1 at this time) spot is also read and set. Then, the scanning controller 41 controls the relevant power supplies so that the scanning magnets 5A, 5B are excited at the current values for the j-th spot.

After the irradiation preparation for the relevant spot has been completed in such a way, the scanning controller 41 outputs a beam extraction start signal in step 300 and controls the RF knockout device 9, thus allowing the ion beam to be extracted from the synchrotron 12. More specifically, the on/off switch 92 is closed by the beam extraction start signal having passed through the accelerator controller 40, and an RF wave is applied to the ion beam from the RF knockout electrode 93, whereupon the ion beam is extracted from the synchrotron 12. Because the scanning magnets 5A, 5B are excited such that the ion beam reaches the position of the first spot, the extracted ion beam is irradiated to the first spot in the relevant slice by the irradiation device 15. When the dose irradiated to the first spot reaches the relevant target dose, the scanning controller 41 outputs a beam extraction stop signal in step 300. The beam extraction stop signal passes through the accelerator controller 40 and closes the on/off switch 92, whereupon the extraction of the ion beam is stopped.

At this time, the irradiation to the first spot in the slice 1 is just completed. Thus, because a determination result in step 208 is "No", the scanning controller 41 shifts to step 209 in which the spot number j is incremented by 1 (namely, the exposure position is moved to an adjacent spot). Then, the above-described processing in steps 205, 208 and 300 is repeated. Stated another way, until the irradiation to all the spots in the slice 1 is completed, the ion beam is irradiated while successively moving the ion beam to the adjacent spot one after another by the scanning magnets 5A, 5B (while the irradiation of the ion beam is stopped during the beam movement) (such process is called spot scanning irradiation).

When the irradiation to the all the spots in the slice 1 is completed, the determination result in step 208 becomes "Yes". At this time, the scanning controller 41 outputs a slice change signal to a CPU in the accelerator controller 40. The CPU in the accelerator controller 40 having received the slice change signal increments the slice number i by 1 (namely, changes the irradiation target to the slice 2) in step 213 and outputs a remaining beam deceleration signal to the synchrotron 12 in step 214. In response to the output of the remaining beam deceleration signal, the accelerator controller 40 controls the power supplies for the various magnets in the synchrotron 12 such that the excitation currents for the magnets are gradually reduced and are finally set to certain preset values, e.g., current values suitable for injection of the ion beam. The ion beam circulating within the synchrotron 12 is thereby decelerated. In this way, a beam extraction enable period differs depending on the number of spots in the slice and the dose irradiated therein. At this time, the irradiation to the slice 1 is just completed and a determination result in step 215 is "No". Therefore, the pattern of accelerator parameters corresponding to the second slice (slice 2) is read and set from the memory in the accelerator controller 40 in step 202. Subsequently, the above-described processing in steps 203-215 is executed for the slice 2. Likewise, the above-described processing in steps 202-215 is executed until the irradiation to all the spots in the slice 4 is completed.

When the determination result in step 215 becomes "Yes" (i.e., when the predetermined irradiation to all the spots in all the slices for the target in the body of the patient 30 is completed), the CPU in the accelerator controller 40 outputs an irradiation terminate signal to the CPU 101.

As described above, the ion beam accelerated in the synchrotron 12 and extracted from the synchrotron 12 is transported through the beam line 4. Then, the ion beam is irradiated to the target in the body of the patient 30 in accordance with the treatment plan through the irradiation device 15 in the treatment room where the patient lies as the irradiation object. On that occasion, the detected signal from the dose monitor 6A disposed in the irradiation device 15 is inputted to the scanning controller 41. The feature of this embodiment resides in the beam dose control based on the integrated dose using that detected signal.

Details of the beam dose control will be described below with reference to FIGS. 6-9.

Figure 6:
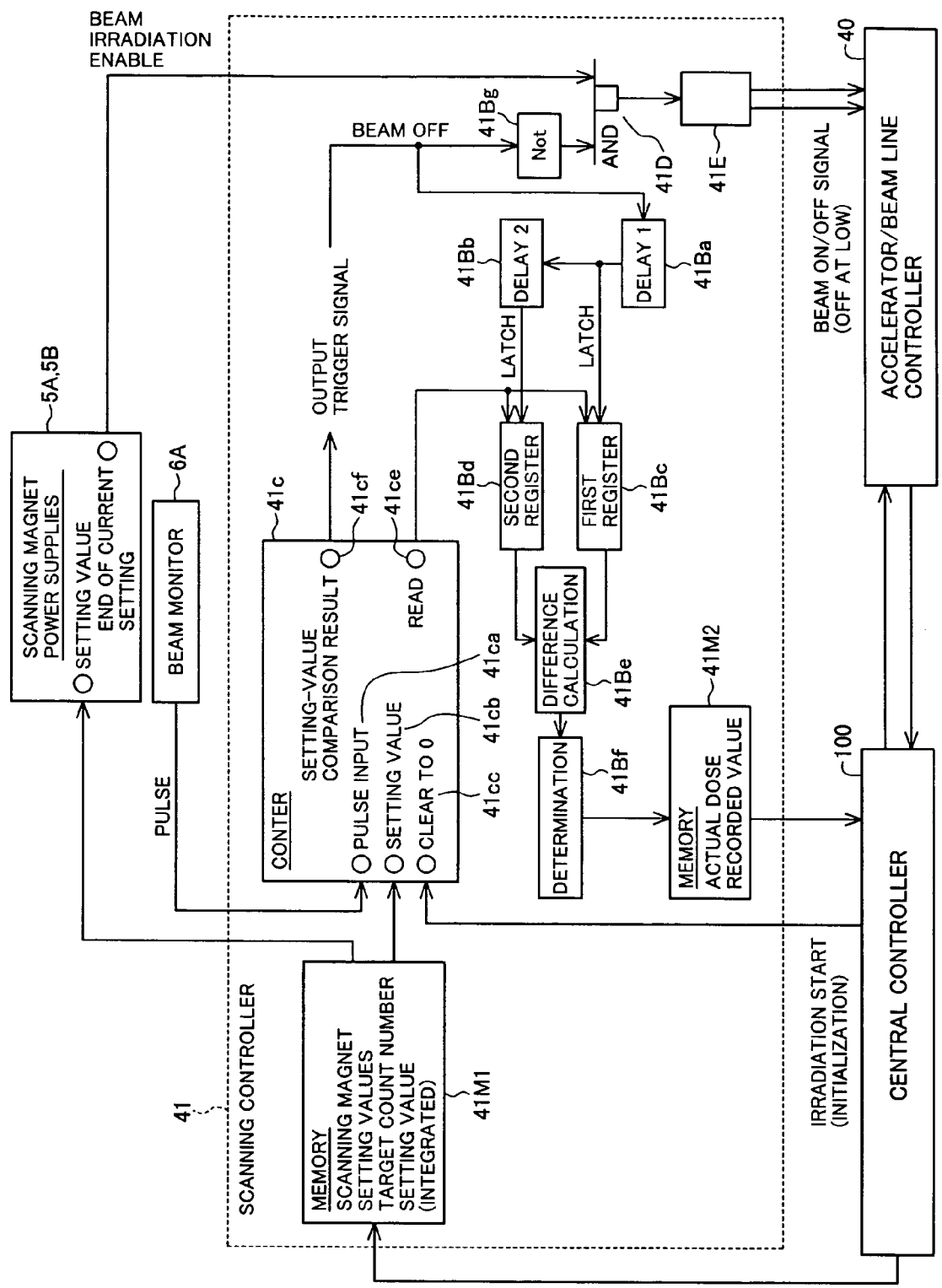
FIG. 6 is a functional block diagram showing details of a functional configuration of the scanning controller in the first embodiment.

FIG. 6 is a functional block diagram showing details of a functional configuration of the scanning controller 41. As shown in FIG. 6, the scanning controller 41 includes a counter 41c as a component related to the dose detection. The dose monitor (beam monitor) 6A is of the known type outputting a pulse depending on the quantity of electrical charges ionized upon the passage of the ion beam. More concretely, the dose monitor 6A outputs one pulse for each small predetermined quantity of the electrical charges. The counter 41c counts the number of pulses outputted from the dose monitor 6A to measure the dose.

In addition to the counter 41c, the scanning controller 41 includes memories 41M1 and 41M2, a first delay timer 41Ba, a second delay timer 41Bb, a first register 41Bc, a second register 41Bd, a difference calculating section 41Be, a determining section 41Bf, a NOT circuit 41Bg, an AND circuit 41D, and a beam on/off signal generator 41E. Also, the counter 41c has a pulse input section 41ca, a setting value input section 41cb, an initialization (clear) signal input section 41cc, a count value read section 41ce, and a setting-value comparison result output section 41cf.

Figure 7:
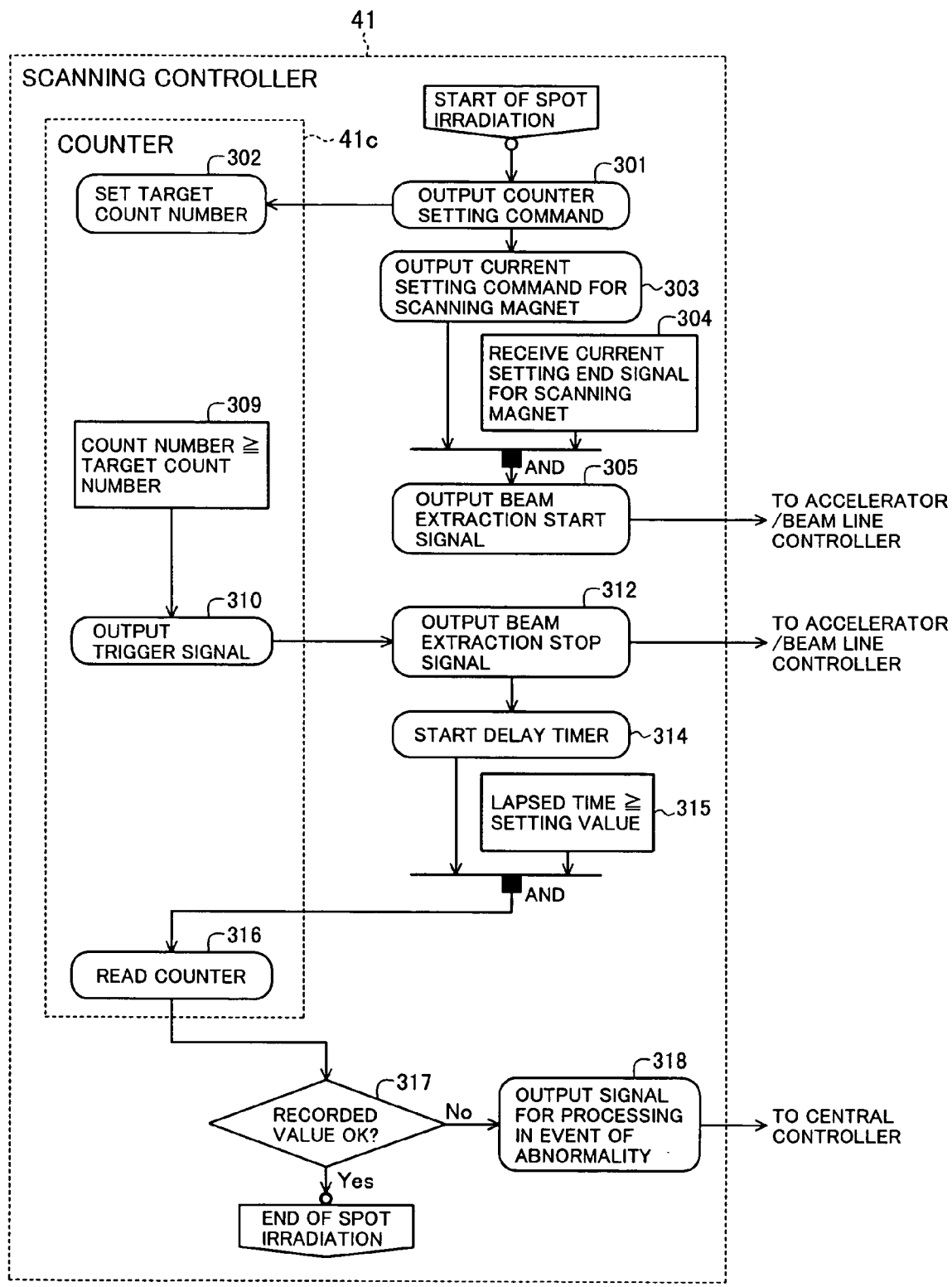
FIG. 7 is a flowchart showing details of the control procedures executed by the scanning controller in the first embodiment.

Detailed procedures executed by the scanning controller 41 in steps 205 and 300 of FIG. 5 will be described below with reference to FIG. 7. As described above, the operator i and the operator j are each initialized to 1 in advance. In step 301, the scanning controller 41 outputs a counter setting command corresponding to the target count number for the counter 41c, which is already stored in the memory 41M1, to the setting value input section 41cb of the counter 41c. In accordance with the counter setting command, the counter 41c sets, in step 302, the target count number for the first spot in the slice 1. The target count number is a value corresponding to the target dose up to the relevant spot in the relevant slice, which is put in column "target dose" of FIG. 4. The target count number is calculated in the scanning controller 41 based on the target dose up to each relevant spot before the start of irradiation of the ion beam for that spot. The calculation of the target count number using the target dose may be executed immediately before the counter 41c receives the counter setting command, or before the central controller 100 transmits data to the scanning controller 41 if the central controller 100 executes that calculation.

After the end of the processing in step 301, the scanning controller 41 advances to step 303 in which the current setting commands for the scanning magnets 5A, 5B (i.e., the current value data put in columns "X-position" and "Y-position" of FIG. 4) corresponding to the relevant spot are outputted to the power supplies for the scanning magnets 5A, 5B. The scanning magnets 5A, 5B generate bending electromagnetic forces in accordance with the relevant current values. To the scanning controller 41, the power supplies for the scanning magnets 5A and 5B output respective current setting end signals each indicating that the current setting has been completed.

On condition that the current setting command is outputted (step 303) and the current setting end signals are inputted from the power supplies for the scanning magnets 5A, 5B (step 304), the scanning controller 41 outputs the beam extraction start signal in step 305. The beam extraction start signal passes through the accelerator controller 40 and reaches the on/off switch 92 to close it. Responsively, the RF power is applied to the RF knockout electrode 93, whereby the ion beam is extracted from the synchrotron 12 and is irradiated to the relevant spot (e.g., the first stop in the slice 1).

When the beam irradiation is started with the output of the beam extraction start signal in step 305, the detected signal from the dose monitor 6A is converted to a train of dose pulses by a current/frequency converter (I/F converter, not shown) and inputted to the counter pulse input section 41ca of the scanning controller 41 for counting the number of the pulses, as described above. The count number represents the dose integrated from the start of the counting.

When the value counted based on the input pulses from the pulse input section 41ca reaches or exceeds a setting value of the target count number set in step 302 (step 309), the counter 41c outputs a trigger signal from the setting-value comparison result output section 41cf in step 310.

In response to the trigger signal, the scanning controller 41 produces the beam extraction stop signal and outputs it to the accelerator controller 40 (step 312). The beam extraction stop signal passes through the accelerator controller 40 and reaches the on/off switch 92. Thus, the scanning controller 41 enables the on/off switch 92 to be controlled essentially by the beam extraction stop signal so that the on/off switch 92 is opened. As a result, the extraction of the ion beam from the synchrotron 12 is stopped and the irradiation of the ion beam to the patient is stopped as described above.

The output of the beam extraction start signal and the beam extraction stop signal from the scanning controller 41 will be described below with reference to FIG. 6. The current setting end signals outputted from the power supplies for the scanning magnets 5A, 5B are inputted to the AND circuit 41D in the scanning controller 41. When the trigger signal is not outputted from the counter 41c in that state, the NOT circuit 41Bg outputs "1" to the AND circuit 41D. When the AND circuit 41D receives the beam extraction stop signal and "1" from the NOT circuit 41Bg, it outputs "1" to the beam on/off signal generator 41E.

When the trigger signal is outputted from the counter 41c, the NOT circuit 41Bg outputs "0" to the AND circuit 41D. When the AND circuit 41D receives "0" from the NOT circuit 41Bg while receiving the beam extraction stop signal, it outputs "0" to the beam on/off signal generator 41E.

The beam on/off signal generator 41E outputs the beam extraction start signal when it receives "1", and outputs the beam extraction stop signal when it receives "0".

The scanning controller 41 includes the first delay timer 41Ba and the second delay timer 41Bb. The trigger signal is inputted as a command signal to start the first delay timer 41Ba (step 314). Then, when the time lapsed from the timer start reaches a predetermined setting time (=first delay time, corresponding to "delay 1" in FIG. 8 described later) which is set in advance, a first delay time arrival signal is outputted to the first register 41Bc (step 315). On condition of the input of both the first delay time arrival signal and the first delay-timer start command signal, the first register 41Bc outputs a counter read signal to the counter 41c in step 316, whereupon the count value at that time is inputted to the first register 41Bc from the count value read section 41ce of the counter 41c. Simultaneously, though not shown in FIG. 7 for the sake of avoiding complicacy, the first delay time arrival signal is also inputted to the second delay timer 41Bb as a command signal to start the second delay timer 41Bb. Then, as with the first delay timer 41Ba, when the time lapsed from the start of the second delay timer 41Bb reaches a predetermined setting time (=second delay time, corresponding to "delay 2" in FIG. 8 described later) which is set in advance, a second delay time arrival signal is outputted to the second register 41Bd. On condition of the input of both the second delay time arrival signal and the second delay-timer start command signal, the second register 41Bd outputs a counter read signal to the counter 41c, whereupon the count value at that time is inputted to the second register 41Bd from the count value read section 41ce of the counter 41c.

The count value inputted to the first register 41Bc and the count value inputted to the second register 41Bd are inputted to the difference calculating section 41Be. The difference calculating section 41Be calculates the difference between both the count values and applies the calculated difference to the determining section 41Bf.

Figure 8:
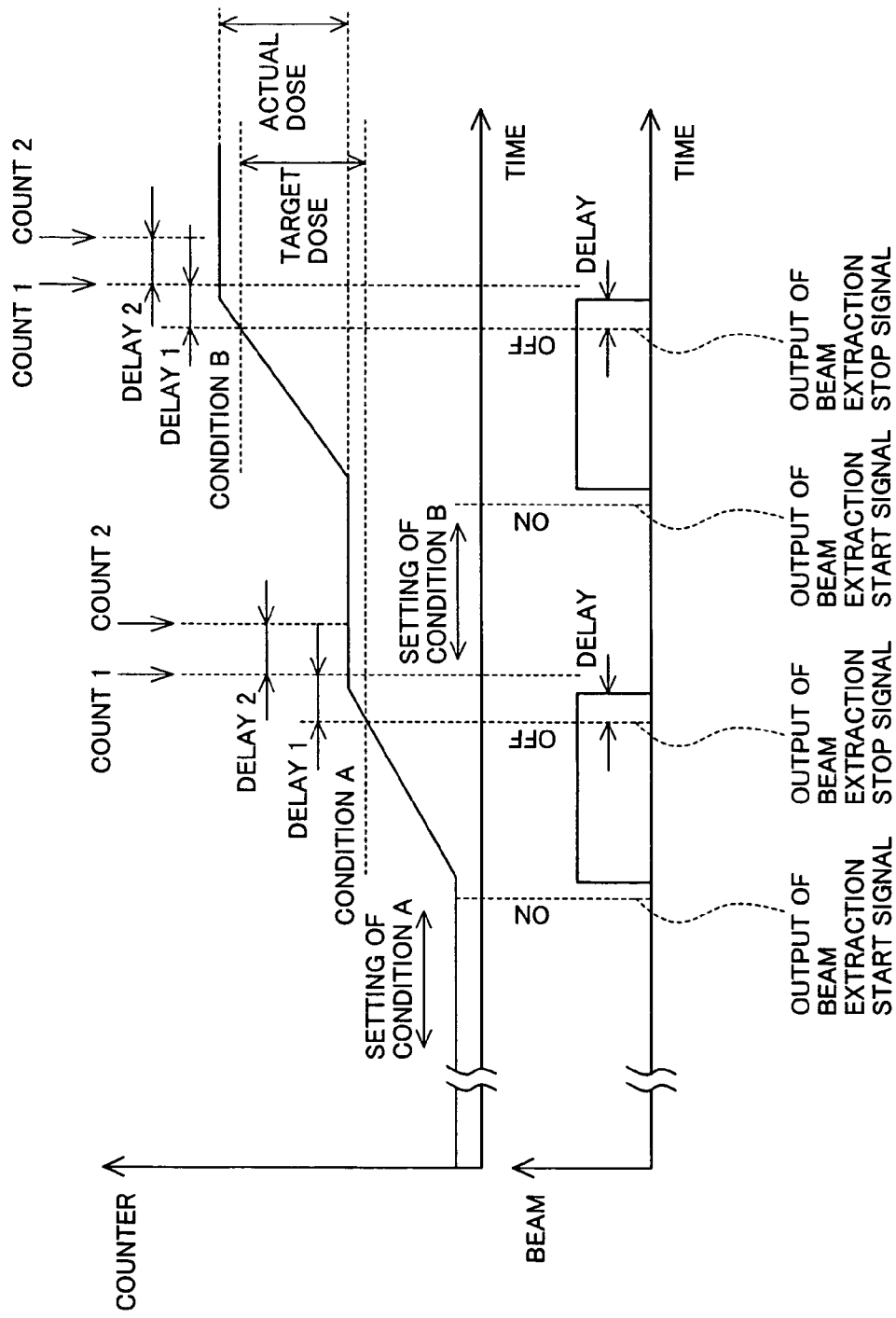
FIG. 8 is a timing chart showing one example of counters and actual beam operation realized with the control procedures, shown in FIG. 7, executed by the scanning controller.

The determining section 41Bf determines whether the count number is a normal value (i.e., whether the calculated difference is within a predetermined proper range) (step 317). If it is determined in step 317 that the count number is an abnormal value, an abnormality signal is outputted to the central controller 100 (step 318). The central controller 100 receives the abnormality signal and executes predetermined processing in the event of the abnormality. If it is determined in step 317 that the count number is the normal value, the count value is stored, as actual dose information, in the memory 41M2 by the determining section 41Bf and then outputted to the central controller 100. The actual dose information may be outputted to the central controller 100 per spot irradiation or in a lot after the end of the irradiations per slice or per unit task. Also, the conversion from the count number to the dose may be executed in the scanning controller 41 or in the central controller 100. FIG. 8 shows, in the form of a timing chart, a series of the above-described operations of the counter 41c.

The thus-constructed particle beam irradiation system of this embodiment has advantages as follows.

In the particle beam irradiation system of the type described above, a dose monitor for measuring dose of the ion beam irradiated to the affected part of the body is usually disposed to minimize exposure of normal tissue to the ion beam and to perform the irradiation treatment in a normal manner without causing excess or deficient dose. In the irradiation to each of the spots, the target dose is set per spot. When an integrated value of the dose measured by the dose monitor reaches the target dose, a beam extraction stop signal (beam stop command) is outputted to the accelerator, whereupon the accelerator stops the extraction of the charged particle beam. On that occasion, there is a possibility that, in the accelerator, a slight response delay occurs after the input of the beam stop command. In the case using a synchrotron that is the accelerator used in this embodiment, ions introduced from a pre-stage accelerator and having low energy are circulated within the synchrotron and accelerated to reach a level of required energy. Then, the circulating charged particle beam having high energy is brought into a resonated state of betatron oscillation, and an RF electromagnetic field is applied to the circulating charged particle beam to increase the betatron oscillation of the charged particle beam in excess of the separatix in resonance, thereby extracting the charged particle beam. Accordingly, even with the beam stop command inputted as mentioned above, the extraction of the charged particle beam is not stopped at once in the strict sense and a slight response delay may occur.

In this embodiment, when the dose counted by the counter 41c based on the output of the dose monitor 61A reaches the target dose (see step 309), the scanning controller 41 outputs, to the RF knockout device 9, a trigger signal serving as a trigger for the output of the beam extraction stop signal (see step 312). At this time, the counter 41c continues the counting even after the output of the beam extraction stop signal without clearing the count number.

FIG. 8 is a timing chart showing behaviors of the counter 41c in that process. As shown in FIG. 8, after the output of the beam extraction stop signal, a response delay may occur until the extraction of the ion beam from the synchrotron 12 is actually stopped (as indicated by "delay" in FIG. 8). During a period (of response delay) from the output of the beam extraction stop signal to the actual stop of the extraction of the ion beam, the dose irradiated as the ion beam extracted from the synchrotron 12 is continuously measured by the dose monitor 6A and is integrated by the counter 41c. After the extraction of the ion beam has been actually stopped, the exposure position is changed to the next one (spot) through the processing of steps 209 and 205 (see FIG. 5), and the target count number (target dose) for the next exposure position is set in step 302 (in FIG. 8, for example, change from a condition A (target dose up to until irradiation to the relevant spot at a certain position is completed) to a condition B (target dose up to until irradiation to the next spot is completed). The target count number means the count number corresponding to the target dose. Further, the scanning magnets 5A, 5B are controlled in accordance with the current setting command outputted in step 303 so that the exposure position of the ion beam is aligned with the next spot. Then, the extraction of the ion beam from the synchrotron 12 is restarted in accordance with the beam extraction start signal in step 305. Here, the count number counted for the next spot contains not only the count number based on the value measured by the dose monitor 6A after the restart of the extraction of the ion beam, but also the count number during a period of response delay from the output of the beam extraction stop signal for the preceding spot to the actual stop of the extraction of the ion beam. In other words, the count number for the next spot is given as a value obtained by setting, as an initial value, the count number counted during the period of response delay with respect to the preceding spot, and by adding up the count number after the restart of the extraction of the ion beam to the initial value. When such a count number for the next spot reaches the target count number (i.e., the dose indicated by "target dose" in FIG. 8), the scanning controller 41 outputs the beam extraction stop signal. Then, the ion beam is further irradiated to the next spot during a subsequent period of response delay. The dose irradiated during the period of response delay with respect to the irradiation for the next spot is substantially equal to the dose irradiated during the period of response delay with respect to the irradiation for the preceding spot (i.e., the above-mentioned initial value). Therefore, the dose actually irradiated to the next spot (i.e., the dose indicated by "actual dose" in FIG. 8) is substantially equal to the target dose. The dose irradiated during the period of response delay with respect to the next spot is set as an initial value for the succeeding spot irradiation after the spot is moved to a further next position, followed by adding up the count number to the thus-set initial value. Thereafter, a similar counting process is repeated in a similar manner.

Figure 9:
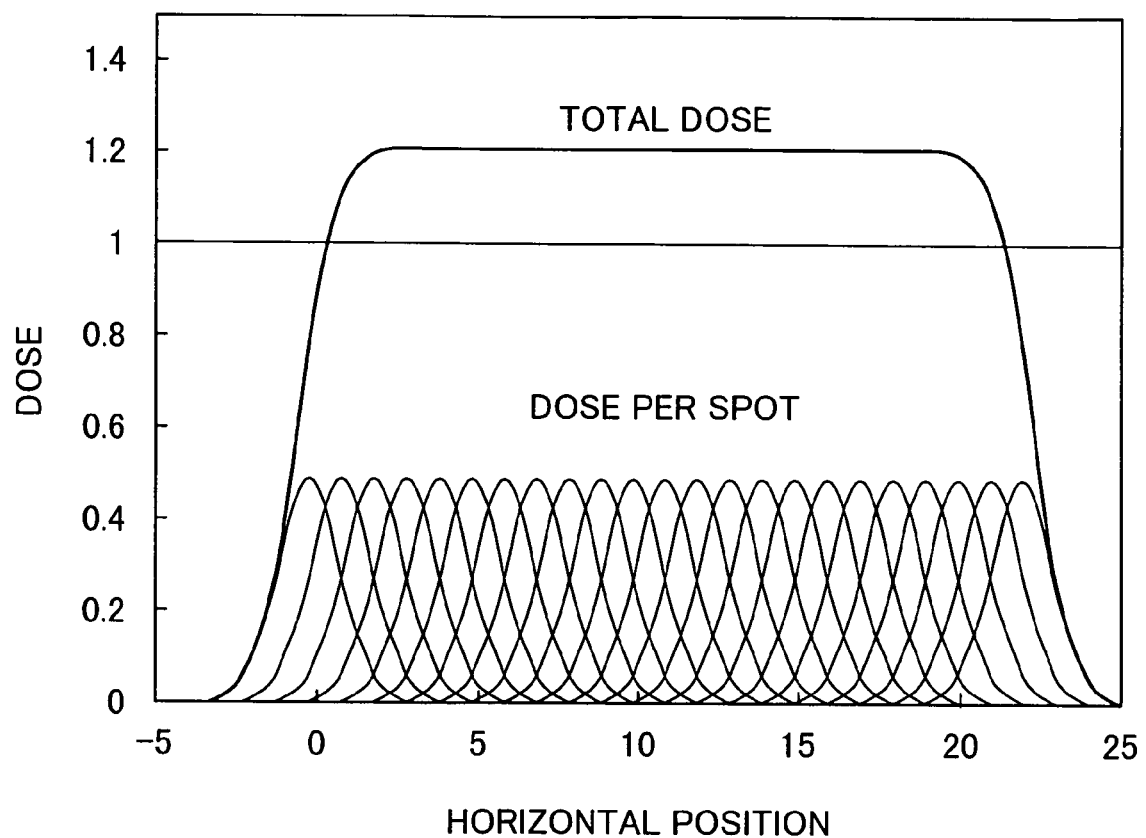
FIG. 9 is a graph showing one example of a dose distribution provided by a comparative example.
Figure 10:
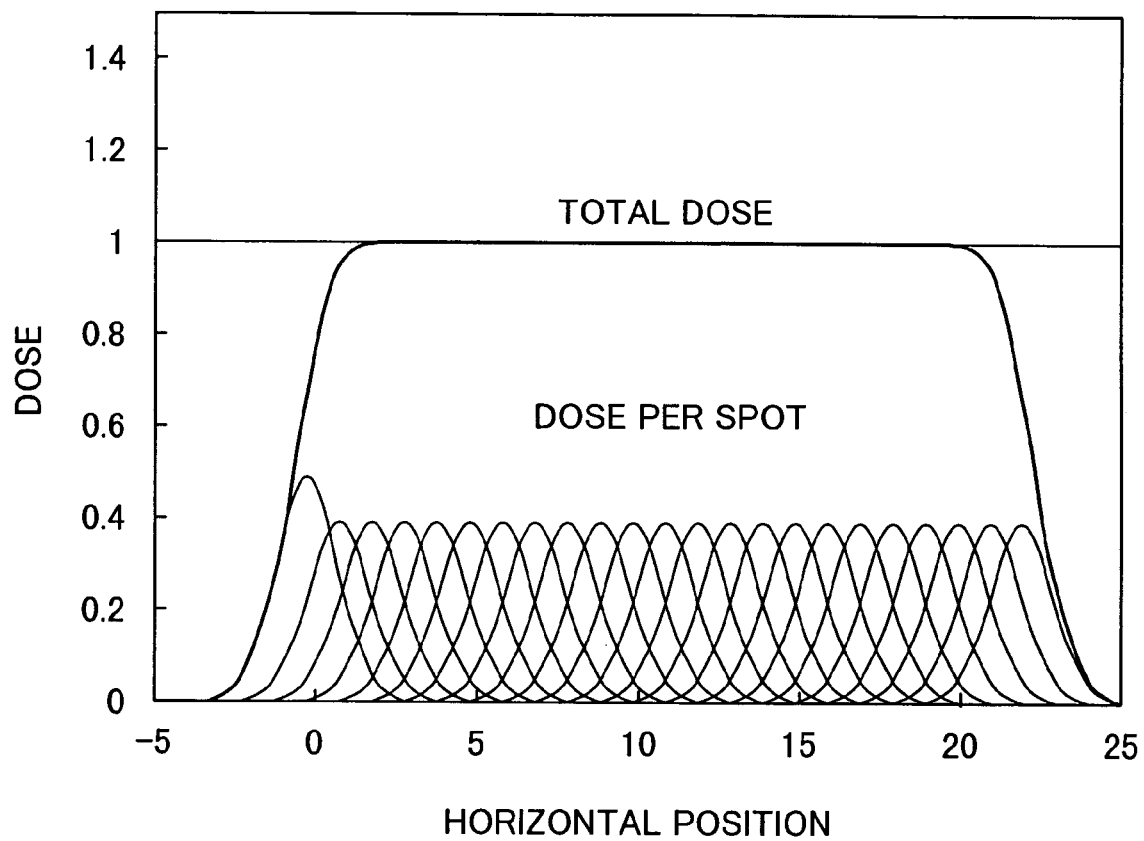
FIG. 10 is a graph showing one example of a dose distribution realized with the control procedures, shown in FIG. 7, executed by the scanning controller.

Thus, because the scanning controller 41 executes the above-described control in accordance with the count number, the irradiation to each spot is performed such that the ion beam is always irradiated to the spot until the dose irradiated to the relevant spot, which includes as the initial value the dose irradiated during the period of response delay with respect to the irradiation for the preceding spot, reaches the target dose for the relevant spot. In the case controlling the dose not taking into account the above-described response delay, as shown in FIG. 9 (in which target total dose is represented by 1.0), there is a possibility that excess irradiation corresponding to the above-mentioned initial value is performed and the target total dose for all the spots becomes 1.2. In contrast, by executing the above-described control in this embodiment, excess irradiation corresponding to the above-mentioned initial value is essentially compensated, as shown in FIG. 10, for all the spots except the spot to which the irradiation is made for the first time (i.e., the spot at the left end in FIG. 10), and the ion beam can be irradiated to each of all the spots except the left-end spot at dose (about 1.0), which is substantially equal to the preset target dose, with high accuracy. As a result, the ion beam can be uniformly irradiated to the affected part of the body (i.e., the irradiation object) and a dose distribution in the affected part of the body can be made uniform.

Also, by executing control to read the dose after the preset delay time (first delay time) has lapsed from the output of the beam extraction stop signal, as described above, the dose irradiated to each spot can be measured with high accuracy even with a response delay occurred when the extraction of the ion beam from the accelerator is stopped.

Further, by executing control to read both the dose after the lapse of the first delay time and the dose at a subsequent point in time after the lapse of the second delay time, and to determine whether the difference between both the doses is not larger than (or smaller than) the predetermined value, it is possible to reliably confirm that the extraction of the ion beam from the accelerator is stopped without failures, and to increase the irradiation accuracy of the ion beam.

Moreover, the scanning controller 41 in this embodiment employs the counter that measures (counts) the integrated value of the dose and continues the counting except when the count number is cleared to 0 at the start of the irradiation. Therefore, neither 0-clearing of the count number nor start/stop control are so frequency performed in the counter, and the counter is less susceptible to malfunction.

Additionally, the controller may be provided with the determining function of calculating the difference between the actual dose and the target dose, and outputting an abnormality signal when the calculated result exceeds a preset allowable range. The provision of the determining function enables the dose of the irradiated ion beam to be monitored and avoided from causing large variations due to the response delay in the accelerator, and also enables an abnormal state of the system to be detected for improvement of safety.

A risk of excess irradiation caused by malfunction of the dose monitor and the counter can be reduced by disposing a plurality of dose monitors and a plurality of counters for integrating doses based on respective outputs of the dose monitors, and by setting the target dose for one of the counters to be larger than the dose planned in the treatment plan. In this case, it is possible to reduce the risk of simultaneous malfunction due to a single failure and to improve safety by operating two or more dose monitors and/or counters with power supplied from separate power supplies, and by increasing independency of individual detection systems through change of respective signal paths.

A proton beam irradiation system according to a second embodiment of the present invention will be described below. The proton beam irradiation system of this second embodiment differs from that of the first embodiment just in the scanning controller. The scanning controller in the proton beam irradiation system of the second embodiment is constituted as a scanning controller 41A shown in FIG. 13. As in the first embodiment, the proton beam irradiation system of this second embodiment comprises the central controller 100, the scanning controller 41A, and the accelerator controller 40, which execute control in a cooperated manner based on the treatment plan information prepared by the treatment planning system 140. As a result of that control, the output of the ion beam from the irradiation device 15 is stopped, and the scanning magnets 5A, 5B are controlled to change the exposure position (spot) of the ion beam in the state where the output of the ion beam is stopped. After the change of the exposure position, the synchrotron 12 and the irradiation device 15 are controlled so as to start the output of the ion beam from the irradiation device 15 again (for the so-called scanning).

Also, as in the first embodiment, the CPU 101 of the central controller 100, shown in FIG. 1, reads the treatment plan information stored in the memory 103 out of the storage 110 and loads the read treatment plan information in the memory (not shown) of the scanning controller 41A. On that occasion, unlike the first embodiment, the target dose for each spot to be transmitted to the scanning controller 41A is the dose separated per spot. Further, as in the first embodiment, the CPU 101 transmits, from among the treatment plan information, the data of operation parameters regarding all the slices (i.e., the degrader numbers and the excitation current values for the various magnets in the beam line which are decided depending on the energy of the ion beam irradiated to each slice) to the accelerator controller 40.

When the spot scanning is performed in this embodiment, the scanning controller 41A and the accelerator controller 40 execute similar control procedures to those shown in FIG. 5. However, because the target dose at each exposure position is not the integrated value as mentioned above, the scanning controller 41A differs from the scanning controller 41 in functional configuration and internal operation.

Figure 12:
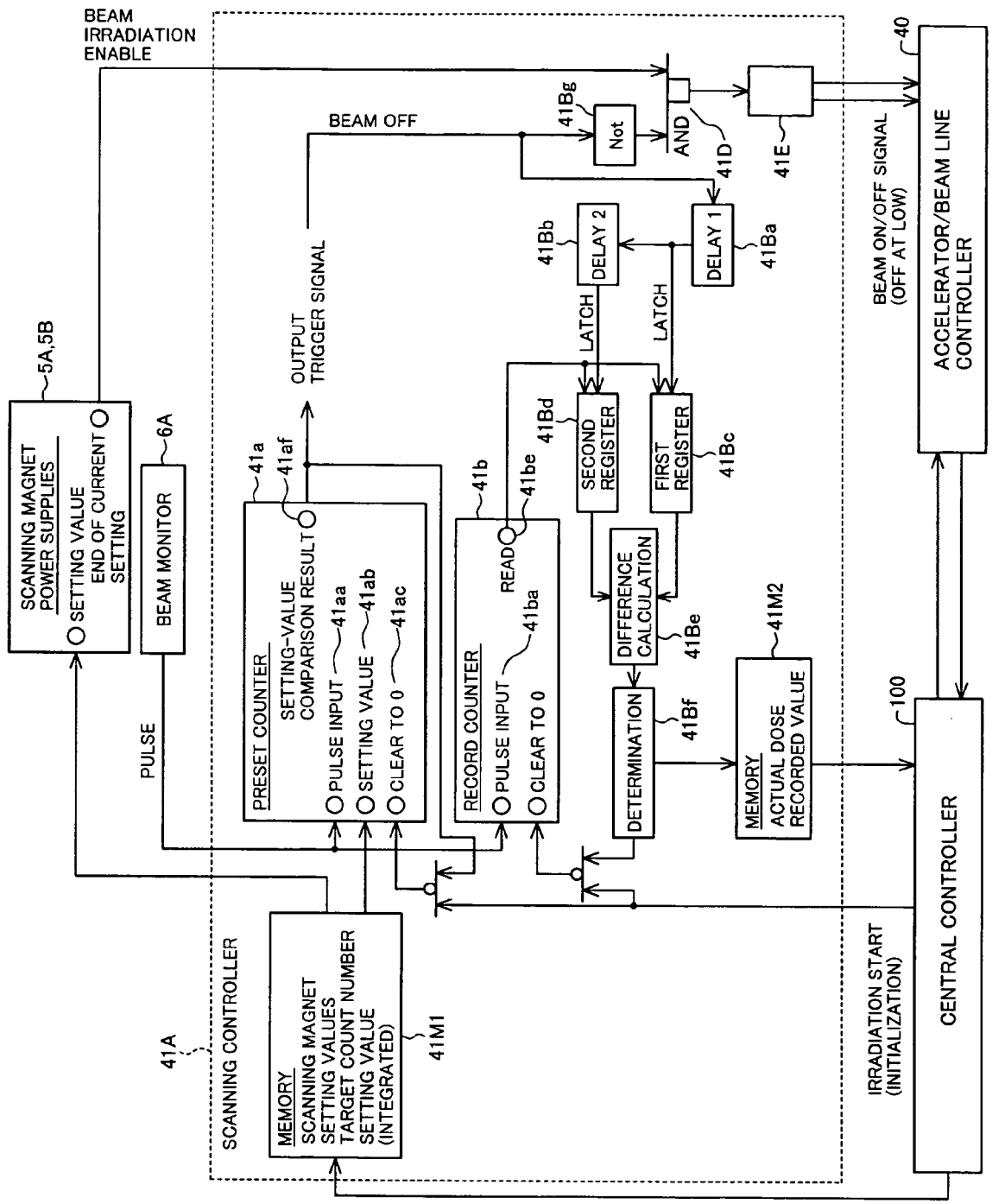
FIG. 12 is a functional block diagram showing details of a functional configuration of the scanning controller in the second embodiment.

FIG. 12 is a functional block diagram showing details of the functional configuration of the scanning controller 41A. As shown in FIG. 12, the scanning controller 41A includes a preset counter 41a and a record counter 41b, which are related to the dose detection. The preset counter 41a and the record counter 41b measure the dose by counting the number of pulses outputted from the dose monitor 6A.

The scanning controller 41A differs from the scanning controller 41 in point of using the preset counter 41a and the record counter 41b instead of the counter 41c. The preset counter 41a has a pulse input section 41aa, a setting value input section 41ab, an initialization (clear) signal input section 41ac, and a setting-value comparison result output section 41af. The record counter 41b has a pulse input section 41ba, an initialization (0-clear) signal input section 41bc, and a count value read section 41be.

Figure 13:
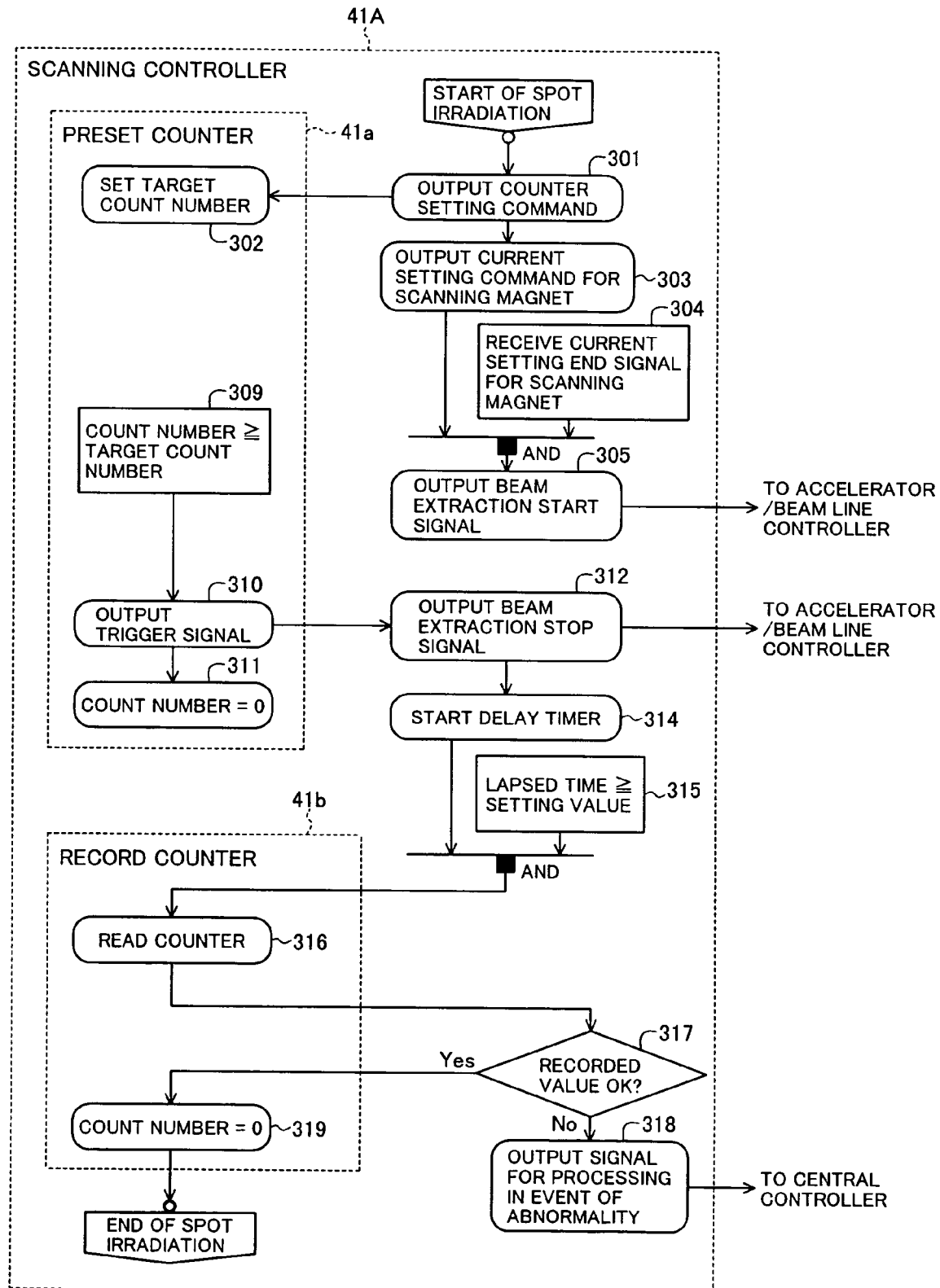
FIG. 13 is a flowchart showing details of the control procedures executed by the scanning controller in the second embodiment.

Detailed procedures executed by the scanning controller 41A in steps 205 and 300 of FIG. 5 will be described below with reference to FIG. 13. Processing in steps 303-305, 312, 314, 315, 317 and 318 is the same as that executed by the scanning controller 41 in those steps. Processing in steps 302 and 309-311 is executed by the preset counter 41a, and processing in steps 316 and 319 is executed by the record counter 41b. The operator i and the operator j are each initialized to 1 in advance. The following description is made of the processing executed by the scanning controller 41A primarily in points differing from the processing executed by the scanning controller 41.

In step 301, the scanning controller 41A outputs a preset counter setting command corresponding to the target count number for the preset counter 41a, which is already stored in the memory 41M1, to the setting value input section 41ab of the preset counter 41a. In accordance with the preset counter setting command, the preset counter 41a sets, in step 302, the target count number for the first spot in the slice 1. The target count number is a value corresponding to the target dose for the relevant spot in the relevant slice, which is put in column "target dose" of FIG. 11.

After the end of the processing in step 301, the scanning controller 41A executes the processing of step 303-305. When the beam irradiation to the patient 30 is started with the output of the beam extraction start signal in step 305, the detected signal from the dose monitor 6A is converted to a train of dose pulses and inputted to each of the pulse input section 41*aa* of the preset counter 41*a* and the pulse input section 41*ba* of the record counter 41*b*. These counters 41*a*, 41*b* count the number of the pulses concurrently. Each count number represents the dose integrated from the start of the counting.

When the number counted based on the detected signal from the dose monitor 6A exceeds the preset target count number (step 309), the preset counter 41*a* outputs a trigger signal from the setting-value comparison result output section 41*af* (step 310). The trigger signal is inputted as a first reset signal to the initialization (0-clear) signal input section 41*ac*, whereby the count number of the preset counter 41*a* is reset to 0 (step 311). After the reset, the preset counter 41*a* starts again the counting based on the detected signal from the dose monitor 6A.

In response to the trigger signal, the scanning controller 41A outputs the beam extraction stop signal in step 312. Consequently, as described above, the extraction of the ion beam from the synchrotron 12 is stopped and the irradiation to the patient is stopped. In such a way, the irradiation of the ion beam is stopped. As in the scanning controller 41, the scanning controller 41A produces the beam extraction start signal and the beam extraction stop signal in the beam on/off signal generator 41E.

In step 314, the scanning controller 41A starts the operation of the first delay timer 41Ba upon the input of the trigger signal. After the lapse of the first delay time, a first delay time arrival signal is outputted to the first register 41Bc (step 315). The first register 41Bc outputs a counter record-counter read signal to the record counter 41*b* in step 316, whereupon the count number at that time is outputted from the count value read section 41*be* to the first register 41Bc. Also, when a counter record-counter read signal is outputted from the second register 41Bd to the record counter 41*b*, the count number at that time is inputted to the second register 41Bd from the count value read section 41*be*. The difference calculating section 41Be calculates the difference between both the count numbers inputted from the first and second registers 41Bc, 41Bd, and the calculated difference is inputted to the determining section 41Bf. The determining section 41Bf determines whether the count number is a normal value (i.e., whether the calculated difference is within a predetermined proper range) (step 317). If the determination result in step 317 is "No", i.e., if it is determined that "the count number is an abnormal value", an abnormality signal is outputted to the central controller 100 in step 318. If it is determined in step 317 that the count number is the normal value, the determining section 41Bf applies a second reset signal for resetting the record counter 41*b* to the initialization (0-clear) signal input section 41*bc* of the record counter 41*b* via an OR circuit, whereupon the record counter 41*b* is reset to start the counting again (step 319). At the same time, the count number is recorded, as actual dose record, in the memory 41M2 by the determining section 41Bf and is then outputted to the central controller 100. The output of the actual dose record to the central controller 100 may be performed per spot irradiation or in a lot after the end of the irradiations per slice or per unit task. Also, the conversion from the count number to the dose may be executed in the scanning controller or in the central controller.

FIG. 14 shows, in the form of a timing chart, a series of the above-described operations of the counters 41*a*, 41*b*.

The thus-constructed particle beam irradiation system of the second embodiment has similar advantages to those obtainable with the first embodiment.

In addition, according to this embodiment, since the count number counted by each of the preset counter and the record counter is decided depending on the dose for each spot, a maximum count number can be made smaller than the case integrating the count for all the spots as in the first embodiment. Therefore, the amount of data transmitted and received between the central controller 100 and the scanning controller can be reduced, and the time required for transmitting and receiving the data can be cut. The control system can be thereby constituted with a smaller-scaled circuit. As a result, it is possible to increase the processing speed in comparison of the count number with the setting value.

In the second embodiment, the dose irradiated during the period of response delay in the synchrotron 12 with respect to the irradiation to a certain spot is assumed to be included in the dose irradiated to the next spot, and based on such an assumption, the ion beam is irradiated to the next spot until reaching the target dose for the next spot. However, the following other methods (1) and (2) can also provide the similar advantages.

(1) In step 309 executed by the preset counter 41*a*, from the target dose for a certain spot, the dose irradiated during the period of response delay with respect to the irradiation to the preceding spot is subtracted, and the count number during the irradiation to the certain spot is further subtracted from the remaining dose. Then, when the remaining dose after the two subtractions becomes 0, the trigger signal is outputted in step 310.

(2) The target count number set by the preset counter in step 302 is given as the dose obtained by subtracting, from the target dose for a certain spot, the dose irradiated during the period of response delay with respect to the irradiation to the preceding spot.

It is to be noted that the irradiation of the ion beam based on the above-described spot scanning is also applicable to a proton beam irradiation system using a cyclotron as the accelerator.

What is claimed is:

1. A particle beam irradiation system comprising:
an accelerator for producing a charged particle beam to be extracted therefrom;
an irradiation device including a charged particle beam scanner and irradiating the charged particle beam extracted from said accelerator to an exposure position of an irradiation object;
a dose detector for measuring a dose of the charged particle beam irradiated to the exposure position; and
a control unit for receiving the dose measured by said dose detector, and when the sum of a first dose irradiated after output of a beam extraction stop signal with respect to a first exposure position preceding a second exposure position and a second dose irradiated to the second exposure position reaches a setting dose, outputting the beam extraction stop signal to stop the extraction of the charged particle beam irradiated to the second exposure position.

2. The particle beam irradiation system according to claim 1, wherein said control unit stops the extraction of the charged particle beam from said accelerator in accordance with the beam extraction stop signal, controls said charged particle beam scanner to change the exposure position to the second exposure position in a state in which the extraction of the charged particle beam is stopped, and after the change of the exposure position, starts the extraction of the charged particle beam from said accelerator in accordance with a beam extraction start signal.

3. The particle beam irradiation system according to claim 1, wherein the dose is a dose integrated from, as an essential start point, start of the irradiation of the charged particle beam to said irradiation object.

4. The particle beam irradiation system according to claim 3, wherein the integrated dose is read when a preset time has lapsed after the output of the beam extraction stop signal.

5. The particle beam irradiation system according to claim 4, wherein a time from the output of the beam extraction stop signal to the read of the integrated dose is longer than a time required for essentially stopping the extraction of the charged particle beam from said accelerator.

6. The particle beam irradiation system according to claim 1, wherein the dose is a dose integrated from, as an essential start point, the output of the beam extraction stop signal.

7. The particle beam irradiation system according to claim 6, wherein the integrated dose is read when a preset time has lapsed after the output of the beam extraction stop signal.

8. The particle beam irradiation system according to claim 7, wherein a time from the output of the beam extraction stop signal to the read of the integrated dose is longer than a time required for essentially stopping the extraction of the charged particle beam from said accelerator.

9. The particle beam irradiation system according to claim 1, wherein said control unit determines the presence of an abnormality based on the dose irradiated to the first exposure position during a period in which a preset time lapses after the output of the beam extraction stop signal.

10. The particle beam irradiation system according to claim 9, wherein a period from the output of the beam extraction stop signal to the lapse of the preset time is longer than the time required for essentially stopping the extraction of the charged particle beam from said accelerator.

11. A particle beam irradiation system comprising:
an accelerator for producing a charged particle beam to be extracted therefrom;
an irradiation device including a charged particle beam scanner and irradiating the charged particle beam extracted from said accelerator to an exposure position of an irradiation object;
a dose detector for measuring a dose of the charged particle beam irradiated to the exposure position; and
a control unit for receiving the dose measured by said dose detector, and when an integrated dose for a second exposure position, including a first dose irradiated after output of a beam extraction stop signal with respect to a first exposure position preceding the second exposure position, reaches a setting dose, outputting the beam extraction stop signal to stop the extraction of the charged particle beam irradiated to the second exposure position.

12. The particle beam irradiation system according to claim 11, wherein said control unit stops the extraction of the charged particle beam from said accelerator in accordance with the beam extraction stop signal, controls said charged particle beam scanner in a state in which the extraction of the charged particle beam is stopped, thereby changing the exposure position to the second exposure position, and after the change of the exposure position, starts the extraction of the charged particle beam from said accelerator in accordance with a beam extraction start signal.

13. The particle beam irradiation system according to claim 11, wherein the dose is a dose integrated from, as an essential start point, start of the irradiation of the charged particle beam to said irradiation object.

14. The particle beam irradiation system according to claim 13, wherein the integrated dose is read when a preset time has lapsed after the output of the beam extraction stop signal.

15. The particle beam irradiation system according to claim 14, wherein a time from the output of the beam extraction stop signal to the read of the integrated dose is longer than a time required for essentially stopping the extraction of the charged particle beam from said accelerator.

16. The particle beam irradiation system according to claim 11, wherein the dose is a dose integrated from, as an essential start point, the output of the beam extraction stop signal.

17. The particle beam irradiation system according to claim 16, wherein the integrated dose is read when a preset time has lapsed after the output of the beam extraction stop signal.

18. The particle beam irradiation system according to claim 17, wherein a time from the output of the beam extraction stop signal to the read of the integrated dose is longer than a time required for essentially stopping the extraction of the charged particle beam from said accelerator.

19. The particle beam irradiation system according to claim 11, wherein said control unit determines the presence of an abnormality based on the dose irradiated to the first exposure position during a period in which a preset time lapses after the output of the beam extraction stop signal.

20. The particle beam irradiation system according to claim 19, wherein a period from the output of the beam extraction stop signal to the lapse of the preset time is longer than the time required for essentially stopping the extraction of the charged particle beam from said accelerator.

* * * * *